(12) United States Patent
Jakoby

(10) Patent No.: US 6,952,951 B2
(45) Date of Patent: Oct. 11, 2005

(54) METHOD AND DEVICE FOR MEASURING THE VISCOSITY OF A LIQUID

(75) Inventor: Bernhard Jakoby, Vienna (AT)

(73) Assignee: Robert Bosch GmbH, Stuttgart (DE)

(*) Notice: Subject to any disclaimer, the term of this patent is extended or adjusted under 35 U.S.C. 154(b) by 24 days.

(21) Appl. No.: 10/399,120
(22) PCT Filed: Aug. 21, 2002
(86) PCT No.: PCT/DE02/03052
§ 371 (c)(1), (2), (4) Date: Sep. 22, 2003
(87) PCT Pub. No.: WO03/019151
PCT Pub. Date: Mar. 6, 2003

(65) Prior Publication Data
US 2004/0025573 A1 Feb. 12, 2004

(51) Int. Cl.$^7$ .............................................. G01N 25/00
(52) U.S. Cl. .................... 73/54.42; 73/53.05; 73/54.02; 73/54.01; 73/54.43
(58) Field of Search ................................ 73/54.42, 54.01, 73/53.05, 54.02, 54.43

(56) References Cited

U.S. PATENT DOCUMENTS 3,479,863 A   11/1969   Kleiss
5,423,302 A    6/1995   Glassey

FOREIGN PATENT DOCUMENTS

DE   100 08 547   8/2001
EP   0 616 204    9/1994
JP   06 129974    5/1994

Primary Examiner—Hezron Williams
Assistant Examiner—André K. Jackson
(74) Attorney, Agent, or Firm—Kenyon & Kenyon

(57) ABSTRACT

A method and a device are proposed for measuring the viscosity of a liquid (12), a conclusion being reached on the temperature of the liquid (12 at the location of the viscosity sensor (20), starting from temperature measurements and/or viscosity measurements made in the past.

12 Claims, 1 Drawing Sheet

METHOD AND DEVICE FOR MEASURING THE VISCOSITY OF A LIQUID

BACKGROUND INFORMATION

Software-based systems, for indicating that an engine oil change in a motor vehicle is required, are known, of which some are based on algorithms which evaluate parameters such as, for instance, the mileage covered since the last oil change or the frequency of cold starts.

Alternatively, other known methods avail themselves of sensor signals which describe the physical state of the oil directly, using suitable sensors, for example, the dielectric constant of the oil or, as a far more reliable quantity, the oil viscosity being measured. In this context, from the determination of the viscosity change of the engine oil since the last oil change, a viscosity-based oil change criterion may be derived, since engine oil breakdown is usually associated with an increase in viscosity. In evaluation electronics having a connected display device in usual systems, for example, a viscosity boundary value may be stored, which is compared to measured viscosity values of the engine oil, and when they exceed it, an instruction is given to the driver as to the next due time for oil change. The physical oil parameters ascertained by these methods known from the related art are temperature-dependent without exception, so that a temperature compensation computation is necessary for the determination. Also, from unpublished Patent Application DE 100 085 47, a method for the assessment of the breakdown of engine oil is known, in which the engine oil viscosity is measured by a sensor, and in which a measuring sensor is allocated to the sensor for the oil viscosity measurement for the simultaneous determination of the oil temperature, the oil viscosity and the oil temperature being measured in the cooling phase of the engine, after it is shut off.

SUMMARY OF THE INVENTION

Compared to this, the method according to the present invention and the device according to the present invention, having the features of the alternative independent claims has the advantage that the oil viscosity can be measured at any time, i.e. not only in the cooling phase of the engine. Moreover, the method according to the present invention and the device according to the present invention are distinguished by the fact that it is advantageously possible to carry out a more accurate determination of the viscosity. For, during the monitoring of liquid operating substances such as engine oil, a viscosity measurement using a viscosity sensor may be drawn upon for assessing the current liquid state. However, since viscosity $\eta$, as a rule, is a strongly temperature dependent quantity, it is imperative simultaneously to determine temperature T by a temperature sensor. A correspondingly ascertained viscosity-temperature measured value pair $\{\eta,T\}$ characterizes a point of the viscosity-temperature characteristic curve $\eta=\eta(T)$ of the liquid. During the recording of several points at various temperatures, which is easily possible if the medium to be monitored is heated and cooled in regular operation, as happens, for instance in the case of engine oil, several measured value pairs may be used for interpolation of the characteristic curve $\eta(T)$. The method according to the present invention, as given in the main claim has the advantage that the viscosity-temperature measured value pairs $\{\eta,T\}$ are determinable with greater accuracy, and are therefore drawn upon for the more accurate characterization of the viscosity-temperature characteristic curve $\eta=\eta(T)$, since the viscosity $\eta$ measured by the viscosity sensor was generally ascertained at a temperature different from the temperature measured by the temperature sensor. The different temperature of the liquid at the location of the viscosity sensor and at the location of the temperature sensor, given rise to by the spatial separation of the viscosity sensor and the temperature sensor, comes about due to a temperature gradient in the liquid. Such a temperature gradient preferably appears when there is a strong heat supply or heat removal in the liquid to be monitored. Therefore the method according to the present invention and the device according to the present invention are advantageously used when there are large temperature gradients, because the viscosity measurements carried out without the method according to the present invention and the device, according to the present invention, in that case would be particularly inaccurate.

The measures specified in the dependent claims permit advantageous further refinements and improvements of the method indicated in the main claim and the device indicated in the alternative independent claim.

BRIEF DESCRIPTION OF THE DRAWING

An exemplary embodiment of the present invention is represented in the drawing, and explained in detail in the following description.

DESCRIPTION OF THE EXEMPLARY EMBODIMENT

Figure 1:
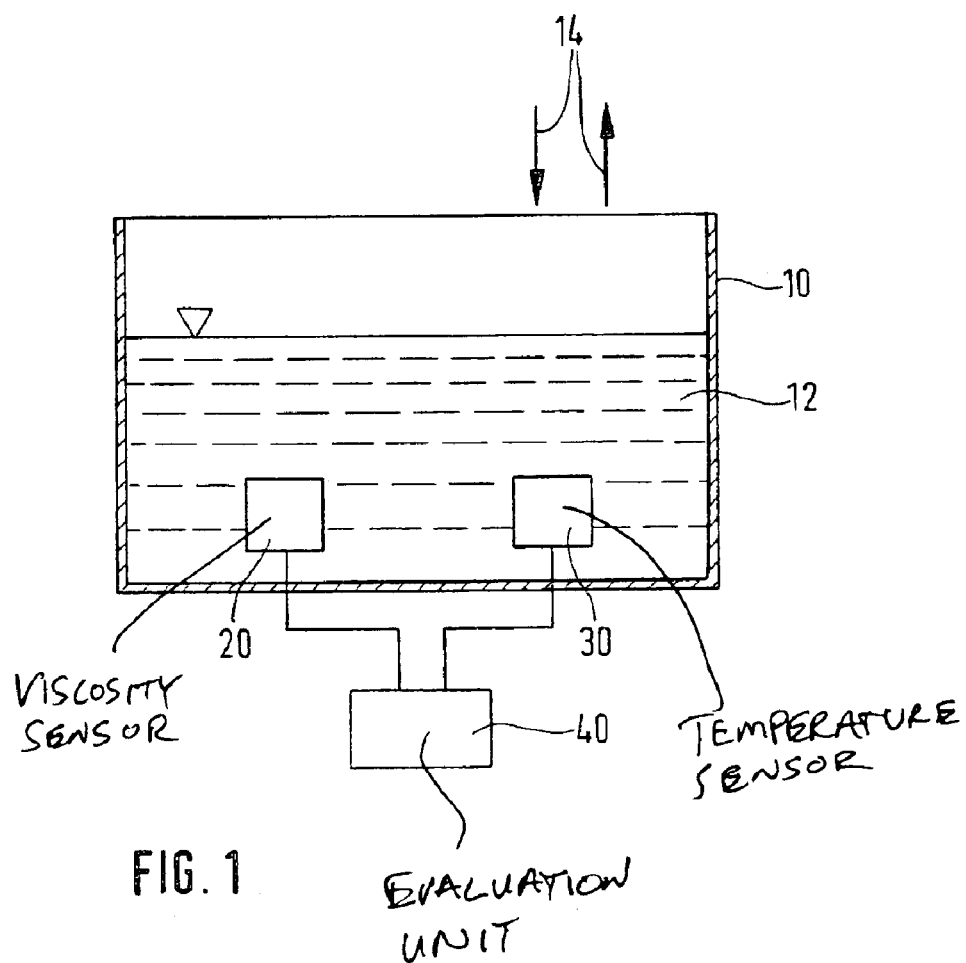
FIG. 1 shows a scheme in principle of the measuring setup.

A container 10 holding a liquid 12 is illustrated in FIG. 1. In container 10, or rather on container 10, a viscosity sensor 20 and a temperature sensor 30 are provided. Both viscosity sensor 20 and temperature sensor 30 are connected to an evaluation unit 40. With the aid of two arrows denoted by reference numeral 14 it is indicated that, operationally conditioned in container 10 shown in FIG. 1, there comes about a supply and/or removal of heat and/or liquid 12. Furthermore, liquid 12 in container 10 can be moved, such as by circulating pumps or even by convection, a temperature gradient being created because of especially cold or especially hot locations of container 10.

If it is assumed that there is a temperature gradient in liquid 12 at a specified time t, then the spatial separation of viscosity sensor 20 from temperature sensor 30 has the effect that the temperature of liquid 12 deviates at the spatial position of viscosity sensor 20 from that at the position of temperature sensor 30. According to that, temperature $T_{30}$ measured by temperature sensor 30 does not represent temperature $T_{20}$ (unknown, in principle) of liquid 12 at the location of viscosity sensor 20.

According to that, viscosity-temperature measured value pairs $\{\eta,T_{30}\}$ can a priori not be drawn upon without error to characterize the viscosity-temperature characteristic curve $\eta=\eta(T)$, since viscosity $\eta$ measured by viscosity sensor 20 was generally not ascertained at a temperature different from $T_{30}$, namely $T_{20}$. However, the present invention describes a method for ascertaining valid measured value pairs.

Such a temperature gradients preferably appear when there is a strong heat supply or heat removal in liquid 12 which is to be monitored. This heat removal or heat supply is shown in FIG. 1 by reference numeral 14 and the corresponding arrows. When the heat supply is omitted, the temperature distribution stabilizes largely by thermal compensation procedures, so that, within the framework of the attempted accuracy, the equation $$T_{30} = T_{20} \text{ holds.}$$

According to the present invention it is provided that an algorithm be used which filters out from a series of plotted measured values, or measured value pairs, those values which may be used, that have sufficient accuracy for ascertaining the viscosity-temperature characteristic curve $\eta(T)$. If one starts from a plot of viscosity measured values $\eta_k$ and temperature measured values $T_{30,k}$ at discrete times $t_k$, as can be done, for example by a microcontroller in evaluation unit 40, then values belonging together at a specified time, e.g. at time $t_k$ may be combined to a measured value triad $M_k = \{\eta_k, T_{30,k}, t_k\}$, the index k indicating both at $\eta$ and at $T_{30}$ that these measured values were measured at the kth measuring point in time. In the most general case, the algorithm ascertains, for the measured value triad which belongs to time $t_k$, a dimension number $Z_k$ or a measure $Z_k$ which estimates the degree of inhomogeneity in the temperature distribution on the basis of the current as well as the last N measured value triad $M_{k-1}$ through $M_{k-N}$, that is, in general $$Z_k = f(M_k, M_{k-1}, \ldots M_{k-N}).$$

Now, the dimension number or the measure is to be defined in such a way that the undershooting of a certain threshold value S or a certain threshold indicates an acceptable reduction in the temperature gradient. In other words: All measured value pairs $\{\eta_k, T_{30,k}\}$ for whose appertaining dimension $$Z_k < S$$

is true, may be regarded with sufficient accuracy as points of the viscosity-temperature characteristic curve $\eta = \eta(T)$.

The physical background of the proposed method is the assumption that, because of the thermal compensating procedures, one may draw conclusions with regard to smaller spatial temperature gradients from temporal changes in the local temperature that are becoming smaller. As an example of this, we give an especially simple example for the construction of $Z_k$. Using the provision $$Z_k = f(M_k, M_{k-1}) = |(T_{30,k} - T_{30,k-1})/(t_{k-1})|$$

the absolute value of the temporal difference quotient of the temperature measured value is ascertained as a measure of the inhomogeneity of the temperature of the liquid. If measure $Z_k$ thus ascertained is less than a specified threshold S, the temperature distribution is regarded as sufficiently homogeneous. In this example, only the current measured value triad and the measured value triad before that in time were considered, that means, N=1 is true. Furthermore, only the temperature measured values were drawn upon for the construction of $Z_k$. Generalizations of this expression, e.g. by evaluation of the change in the measured viscosity value, in order to evaluate the temperature changes at the location of viscosity sensor 20 indirectly, and consideration of several value triads lying in the past, are also provided by the present invention.

The present invention also provides that measured value triads be corrected instead of just filtered out. This is carried out with particular advantage if the heating/cooling mechanism of the liquid is very well studied and known, and the formation of corresponding temperature gradients is studied more thoroughly. For example, it is provided according to the present invention that one may conclude from a measured temporal temperature change that there was a corresponding error $$\epsilon = T_{20} - T_{30}$$

and correct measured value $T_{30}$ accordingly.

In order to evaluate the temperature gradients, a plurality of temperature sensors 30 may also be applied spatially separated. In this case, instead of the single temperature sensor 30 shown in FIG. 1, a plurality of such temperature sensors are provided at various locations, particularly of container 10, according to the present invention. Thereby the temperature may be estimated at the location of viscosity sensor 20, for example, by averaging.

What is claimed is:

1. A method for measuring a viscosity of a liquid as a function of a temperature of the liquid, the method comprising:
   providing a viscosity sensor at a first location of the liquid;
   providing at least one temperature sensor at a second, different location of the liquid;
   performing at least one of the following:
   (a) reaching a conclusion on the temperature of the liquid at the first location of the viscosity sensor at a specified point in time, and
   (b) reaching a conclusion on the viscosity of the liquid at the second location of the temperature sensor at a specified point in time; and
   discarding a measured value of at least one of the viscosity sensor and the temperature sensor if a measure of an inhomogeneity of the temperature of the liquid exceeds a specified threshold,
   wherein the at least one of (a) and (b) is performed starting from at least one of the following:
   (1) at least one of temperature measurements and viscosity measurements made in the past, and
   (2) a plurality of temperature measurements at different locations at the specified point in time.

2. A method for measuring a viscosity of a liquid as a function of a temperature of the liquid, the method comprising:
   providing a viscosity sensor at a first location of the liquid;
   providing at least one temperature sensor at a second, different location of the liquid;
   performing at least one of the following:
   (a) reaching a conclusion on the temperature of the liquid at the first location of the viscosity sensor at a specified point in time, and
   (b) reaching a conclusion on the viscosity of the liquid at the second location of the temperature sensor at a specified point in time; and
   correcting a measured value of at least one of the viscosity sensor and the temperature sensor as a function of a measure of an inhomogeneity of the temperature of the liquid,
   wherein the at least one of (a) and (b) is performed starting from at least one of the following:
   (1) at least one of temperature measurements and viscosity measurements made in the past, and
   (2) a plurality of temperature measurements at different locations at the specified point in time.

3. The method according to claim 1, further comprising drawing upon a temporal difference quotient of at least one of the temperature and the viscosity as the measure of the inhomogeneity of the temperature of the liquid.

4. The method according to claim 2, further comprising drawing upon a temporal difference quotient of at least one of the temperature and the viscosity as the measure of the inhomogeneity of the temperature of the liquid.

5. The method according to claim 1, further comprising ascertaining the measure of the inhomogeneity of the temperature of the liquid from a temporal pattern of at least one of the measured temperature and the viscosity of the liquid.

6. The method according to claim 2, further comprising ascertaining the measure of the inhomogeneity of the temperature of the liquid from a temporal pattern of at least one of the measured temperature and the viscosity of the liquid.

7. A device for measuring a viscosity of a liquid as a function of a temperature of the liquid, the device comprising:

a viscosity sensor situated at a first location of the liquid;

at least one temperature sensor situated at a second, different location of the liquid;

an arrangement for discarding a measured value of at least one of the viscosity sensor and the temperature sensor if a measure of an inhomogeneity of the temperature of the liquid exceeds a specified threshold; and means for performing at least one of the following:

(a) reaching a conclusion on the temperature of the liquid at the first location of the viscosity sensor at a specified point in time, and (b) reaching a conclusion on the viscosity of the liquid at the second location of the temperature sensor at a specified point in time, wherein the at least one of (a) and (b) is performed starting from at least one of the following:

(1) at least one of temperature measurements and viscosity measurements made in the past, and (2) a plurality of temperature measurements at different locations at the specified point in time.

8. The device according to claim 7, wherein a temporal difference quotient of at least one of the temperature and the viscosity is drawn upon as the measure of the inhomogeneity of the temperature of the liquid.

9. The method according to claim 7, wherein the measure of the inhomogeneity of the temperature of the liquid is ascertained from a temporal pattern of at least one of the measured temperature and the viscosity of the liquid.

10. A device for measuring a viscosity of a liquid as a function of a temperature of the liquid, the device comprising:

a viscosity sensor situated at a first location of the liquid;

at least one temperature sensor situated at a second, different location of the liquid;

an arrangement for correcting a measured value of at least one of the viscosity sensor and the temperature sensor as a function of a measure of an inhomogeneity of the temperature of the liquid; and means for performing at least one of the following:

(a) reaching a conclusion on the temperature of the liquid at the first location of the viscosity sensor at a specified point in time, and (b) reaching a conclusion on the viscosity of the liquid at the second location of the temperature sensor at a specified point in time, wherein the at least one of (a) and (b) is performed starting from at least one of the following:

(1) at least one of temperature measurements and viscosity measurements made in the past, and (2) a plurality of temperature measurements at different locations at the specified point in time.

11. The device according to claim 10, wherein a temporal difference quotient of at least one of the temperature and the viscosity is drawn upon as the measure of the inhomogeneity of the temperature of the liquid.

12. The method according to claim 10, wherein the measure of the inhomogeneity of the temperature of the liquid is ascertained from a temporal pattern of at least one of the measured temperature and the viscosity of the liquid.

* * * * *

UNITED STATES PATENT AND TRADEMARK OFFICE
CERTIFICATE OF CORRECTION

| | |
|---|---|
| PATENT NO. | : 6,952,951 B2 |
| APPLICATION NO. | : 10/399120 |
| DATED | : October 11, 2005 |
| INVENTOR(S) | : Bernhard Jakoby |

It is certified that error appears in the above-identified patent and that said Letters Patent is hereby corrected as shown below:

(57) Abstract:

Line 1, delete "are proposed"

Line 2, change "a liquid (12)." to --a liquid.--

Line 3, delete "(12"

Line 4, change "(20)," to --sensor,--

Column 1, lines 28-29, change "Patent Application DE" to --German Patent Application No. DE--

Column 1, line 40, change "Compared to this, the method" to --The method--

Column 2, line 16, change "the device, according to the present invention," to --the device according to the present invention--

Column 2, lines 18-21, delete "the measures specified in the dependent claims permit advantageous further refinements and improvements of the method indicated in the main claim and the device indicated in the alternative independent claim."

Column 2, lines 25-27, delete "An exemplary embodiment of the present invention is represented in the drawing, and explained in detail in the following description."

Column 2, lines 31-32, change "DESCRIPTION OF THE EXEMPLARY EMBODIMENT" to --DETAILED DESCRIPTION--

UNITED STATES PATENT AND TRADEMARK OFFICE
CERTIFICATE OF CORRECTION

PATENT NO. : 6,952,951 B2
APPLICATION NO. : 10/399120
DATED : October 11, 2005
INVENTOR(S) : Bernhard Jakoby It is certified that error appears in the above-identified patent and that said Letters Patent is hereby corrected as shown below:

Column 3, line 37, change "of the proposed method" to --of the method--

Signed and Sealed this

Fifteenth Day of May, 2007

JON W. DUDAS
*Director of the United States Patent and Trademark Office*